(12) United States Patent
Schindler et al.

(10) Patent No.: US 6,358,231 B1
(45) Date of Patent: Mar. 19, 2002

(54) TRANSDERMAL ANESTHETIZING SOLUTION AND METHOD AND APPARATUS FOR ANESTHETIZING THE EAR CANAL AND TYMPANIC MEMBRANE

(75) Inventors: Robert A. Schindler, San Francisco, CA (US); Milton Waner, Little Rock, AR (US)

(73) Assignee: Biopolymer, Inc., Newbury Park, CA (US)

( * ) Notice: Subject to any disclaimer, the term of this patent is extended or adjusted under 35 U.S.C. 154(b) by 0 days.

(21) Appl. No.: 09/378,924

(22) Filed: Aug. 23, 1999

Related U.S. Application Data (60) Provisional application No. 60/097,613, filed on Aug. 24, 1998.

(51) Int. Cl.$^7$ .......................... A61M 35/00; A61F 13/20
(52) U.S. Cl. .............................. 604/289; 604/1; 604/2; 604/11; 604/290
(58) Field of Search ................................. 604/1–3, 289, 604/290, 295, 305, 306, 904, 11–18, 216, 218, 185, 187; 606/106, 107; 128/898

(56) References Cited

U.S. PATENT DOCUMENTS

| | | | |
|---|---|---|---|
| 2,737,953 A | | 3/1956 | Wiltein |
| 3,054,403 A | * | 9/1962 | Baker .......................... 128/232 |
| 3,811,437 A | | 5/1974 | Gardner, Jr. |
| 3,896,801 A | | 7/1975 | Grout |
| 4,006,796 A | | 2/1977 | Coehorst |
| 4,034,759 A | | 7/1977 | Haerr |
| 4,724,922 A | | 2/1988 | Kalayjian |
| 5,074,375 A | | 12/1991 | Grozil |
| 5,107,861 A | | 4/1992 | Narboni |
| 5,300,018 A | | 4/1994 | Walsh et al. |
| 5,440,082 A | | 8/1995 | Claes |
| 5,476,446 A | | 12/1995 | Arenburg |
| 5,484,426 A | | 1/1996 | Yoon |
| 5,954,682 A | * | 9/1999 | Petrus ........................... 604/1 |

OTHER PUBLICATIONS

"A Safe, Effective Anesthetic Technique for Outpatient Myringotomy Tube Placement", Carrasco et al., How I Do It, Otology and Neurotology, A Specific Issue and Its Solution, Laryngoscope 103: Jan. 1993.

* cited by examiner

*Primary Examiner*—Kim M. Lewis
(74) *Attorney, Agent, or Firm*—Pillsbury Winthrop LLP; Karry W. Wang (57) ABSTRACT

A topical anesthetic solution includes a tetracaine base dissolved in a solvent, such as isopropyl alcohol. A method for anesthetizing the ear canal and tympanic membrane using the anesthetic solution includes providing a dry, expandable applicator which expands as it absorbs a fluid and inserting the applicator, dry or partially wetted, into the ear canal and advancing the applicator into the ear canal to the vicinity of the tympanic membrane. The applicator is then fully wetted with the anesthetic solution, causing the applicator to fully expand within the ear canal, and is left in the ear canal for a period sufficient to effect anesthesia of the ear canal and tympanic membrane. An apparatus for applying a topical anesthetic to the ear canal and tympanic membrane includes an expandable, absorbent applicator that expands when soaked with a liquid, an applicator withdrawal tether attached to the applicator, and an applicator inserting and soaking device. The inserting and soaking device includes an elongated portion constructed and arranged to insert the applicator, releasably secured to the end thereof, into the ear canal, a fluid conduit defined within the inserting device, a fluid reservoir in fluid communication with the conduit, and a fluid forcing mechanism constructed and arranged to force fluid from the fluid reservoir into the conduit to wet the applicator. A kit for anesthetizing the ear canal includes an absorbent, expandable applicator with a withdrawal tether attached thereto, a gripping and inserting device for gripping the applicator and inserting it into the ear canal, and a fluid injecting device for injecting fluid into the ear canal to soak the applicator.

11 Claims, 5 Drawing Sheets

TRANSDERMAL ANESTHETIZING SOLUTION AND METHOD AND APPARATUS FOR ANESTHETIZING THE EAR CANAL AND TYMPANIC MEMBRANE

This application claims the benefit of prior filed provisional application No. 60/097,613, filed Aug. 24, 1998, which is hereby incorporated by reference.

BACKGROUND

The present invention relates to a method and apparatus for delivering a topical anesthetic solution to the ear canal and tympanic membrane for anesthetizing the ear canal and the tympanic membrane in a manner that is safe, relatively quick, inexpensive, and painless.

Anesthetizing certain regions of the body presents inherent difficulties. In certain instances, anesthetizing procedures can be more expensive, painful, invasive, and/or cumbersome than the simple medical procedures for which the anesthesia is needed. For example, the ear canal is an extremely sensitive structure often requiring local or general anesthesia in order to perform relatively simple procedures, such as removing a foreign body or incising the eardrum to evacuate fluid and place a ventilating tube. It has been estimated that there are more than 1.5 million myringotomies performed in the United States every year, and many are performed on completely anesthetized children. Other simple procedures typically performed on the skin, such as insertion of an intravenous tube, mole removal, or laser removal of skin lesions can require or benefit from the application of a local anesthetic at the site of the procedure.

Use of a general anesthetic raises the cost of the procedure, and requires the presence of many highly skilled medical professionals. In these cases, care shifts by necessity from a physician's office to an out-patient surgical center or hospital, thus further raising the cost of the procedure.

Conventional topical anesthetics do not penetrate the skin of the ear canal without the use of an iontophoreseis device that requires the placement of electrodes near the ear and the passage of an electrical current therethrough. Topically applied EMLA's (Eutectic Mixture of Local Anesthetics), typically available in a cream form, are difficult to place in and remove from the ear canal.

Tetracaine (2-dimethylamino-ethyl-p-butylaminobenzoate, $CH_3(CH_2)_3NHC_6H_4COOCH_2CH_2N(CH_3)_2$) is a known anesthetic agent that is used in various formulations. Tetracaine is available in powder form and is typically dissolved in a solution with a solvent of buffered saline. As an anesthetic, Tetracaine is much more potent than other commonly used anesthetic agents, such as Cocaine or Novocaine, and it is stable at sterilizing temperatures. After application of a Tetracaine-based anesthetic, anesthesia can be effected in about 15 minutes to one hour and can last for up to 1½–3 hours. On the other hand, Tetracaine is also significantly more toxic than other anesthetics. For this reason, tetracaine is not used internally or in mucosal areas unless at very low dosages. For example, solution concentrations on the order of 0.5% Tetracaine have been used in ophthalmic applications, concentrations of 1 to 2% have been used in the mouth or nose and applied as a spray, and 0.1 to 0.5% solutions have been used in spinal or epidural applications. At such low concentrations, however, even tetracaine-based anesthetics have limited effectiveness in topical applications. Moreover, anesthetic solutions of Tetracaine and saline have poor transdermal effectiveness, except in mucosal tissues.

Presently, a topical anesthetic gel containing tetracaine is commercially available in the United Kingdom from Smith and Nephew Healthcare Ltd. under the trade name Ametop Gel. The gel can be applied topically to the skin where it is purported to prevent needle pain by promoting passive diffusion of a local anesthetic drug through the skin barrier, where it blocks the underlying pain receptors. Also, a topical anesthetic spray containing Tetracaine and indicated for production of anesthesia of accessible mucous membranes is presently available from Cetylite Industries, Inc. under the tradename Cetacaine®.

Ametop Gel is not particularly suited for ear canal applications, because gels are difficult to place in and remove from the ear. Cetacaine® is effective only on mucosal tissues, such as the mouth and nose.

Carrasco et al. describe a technique for anesthetizing the tympanic membrane using a solution of about 80 mg of tetracaine base dissolved in about 20 drops of isopropyl alcohol. Carrasco, Vincent, N., et al., *A Safe, Effective Anesthetic Technique for Outpatient Myringotomy Tube Placement, Laryngoscope* 103: January 1993, pp 92–93. A cottonoid is moistened with the solution and is placed on the tympanic membrane for about 15 minutes using an alligator forceps. One potential problem with such a technique, however, is that, because the solvent is alcohol, the solution can evaporate before anesthesia is complete. Furthermore, the moistened cottonoid, being relatively soft and limp, may not maintain sufficient pressure with the tympanic membrane and the walls of the ear canal to properly effect anesthesia.

The need exists, therefore, for a safe, effective, and cost-effective apparatus and method for anesthetizing surface tissues of the body and, in particular, the ear canal and tympanic membrane.

SUMMARY OF THE INVENTION

The invention, in one form, is a solution comprising 8–20% tetracaine and 70–80 wt % isopropyl alcohol. A stabilizer and a preservative may be added to the solution.

In another form, the invention is an apparatus for applying a fluid topical anesthetic to the ear canal and tympanic membrane. The apparatus comprises an expandable absorbent applicator, which is maintained in a compressed configuration when in a dry state and which expands when in a fluid-soaked state. An applicator withdrawal tether is attached to the applicator to facilitate withdrawal of the applicator from an ear canal into which the applicator has been inserted. An applicator inserting and soaking device includes an elongated insertion portion defining a fluid conduit therein, a fluid reservoir, and a fluid forcing mechanism for forcing fluid from the reservoir through the conduit. The applicator is releasably secured to a distal end of the insertion portion for inserting the applicator into an ear canal, and fluid can be forced from the reservoir, through the conduit, and out the distal end to soak the applicator.

In yet another form, the invention is a method of anesthetizing the ear canal and the tympanic membrane using a topical anesthetic solution. The method comprises providing an expandable absorbent applicator in a dry, compressed condition, the applicator being constructed and arranged to expand when wetted. An anesthetic solution, comprising Tetracaine dissolved in a solvent, is provided, and the applicator is inserted in a dry, compressed condition or a partially wetted, partially expanded condition into the ear canal and is advanced to a position contacting or adjacent to the tympanic membrane. The entire applicator is wetted with the anesthetic solution to cause the applicator to fully expand, so that an outer surface of the applicator and the anesthetic solution absorbed by the applicator are in contact with the inner walls of the ear canal and the tympanic membrane, and the expanded applicator is left in the ear canal for a period of time sufficient to attain a desired level of anesthetization of the ear canal and tympanic membrane. After the desired level of anesthetization is attained, the applicator is withdrawn from the ear canal.

In yet another form, the invention comprises a set of instruments useful for anesthetizing the ear canal and the tympanic membrane with a topical anesthetic solution. The set comprises an absorbent applicator, an applicator gripping and inserting device, and a fluid injecting device. The applicator is initially in a dry, compressed condition and is constructed and arranged to expand when wetted. The applicator gripping and inserting device is adapted to grip the applicator and insert it into the ear canal therewith. The fluid-injecting device includes a reservoir for containing an amount of topical anesthetic solution and is adapted to inject topical anesthetic solution from the reservoir to the applicator inserted into the ear canal where it is absorbed by the applicator, thereby causing the applicator to expand within the ear canal so that an outer surface of the applicator and the anesthetic solution absorbed by the applicator are in contact with the inner walls of the ear canal and the tympanic membrane.

BRIEF DESCRIPTION OF THE DRAWINGS

Preferred features and characteristics of the present invention, as well as the methods of operation of the invention and the function and interrelation of the elements of structure, will become more apparent upon consideration of the following description and the appended claims with reference to the accompanying drawings (wherein like reference numerals designate corresponding parts in the various figures) of which:

DETAILED DESCRIPTION OF THE PREFERRED EMBODIMENT

The anesthetic agent of the present invention is an amino ester local anesthetic comprising 8–20%, and most preferably about 16%, Tetracaine base (2-dimethylamino-ethyl-p-butylaminobenzoate, $CH_3(CH_2)_3NHC_6H_4COOCH_2CH_2N(CH_3)_2$) dissolved in a suitable solvent. Most alcohols constitute a preferred solvent and isopropyl alcohol in a proportion of 70 to 80% constitutes a most preferred solvent. Tetracaine-alcohol solutions have been found to have good transdermal effectiveness for producing anesthesia in non-mucosal tissues, especially within the ear canal. The relatively high concentration of alcohol is preferred so that the alcohol in the solution will dissolve the dead skin outer layer of the epidermis and thereby facilitate absorption of the tetracaine anesthetic. In addition, alcohol-based Tetracaine solutions can also have tissue cleansing effects, especially in the ear canal where the alcohol dissolves ear wax. An alcohol formulation would, however, have limited effectiveness in mucosal tissue, because alcohol may cause burning of the mucosal tissue.

If the anesthetic is provided in an unmixed state, that is, the Tetracaine powder and associated solvent are contained in separate vessels and are mixed into solution only immediately before application, a preservative and stabilizer are not necessary. On the other hand, if the solution of Tetracaine and solvent is pre-mixed, a preservative and a stabilizer, such as benzalkonium chloride, are preferably added to the solution.

To effect local anesthesia, the Tetracaine-based anesthetic solution is applied to the surface of the region to be anesthetized. Full anesthetization can take anywhere from 10 to 30 minutes of contact of the solution with the indicated region. Because the solvent employed in the solution is preferably an alcohol, the solution is prone to rapid evaporation. Accordingly, application of the solution is preferably effected in a manner that will keep the region to be anesthetized "wet" with anesthetic solution for the prescribed anesthetizing period.

Figure 1:
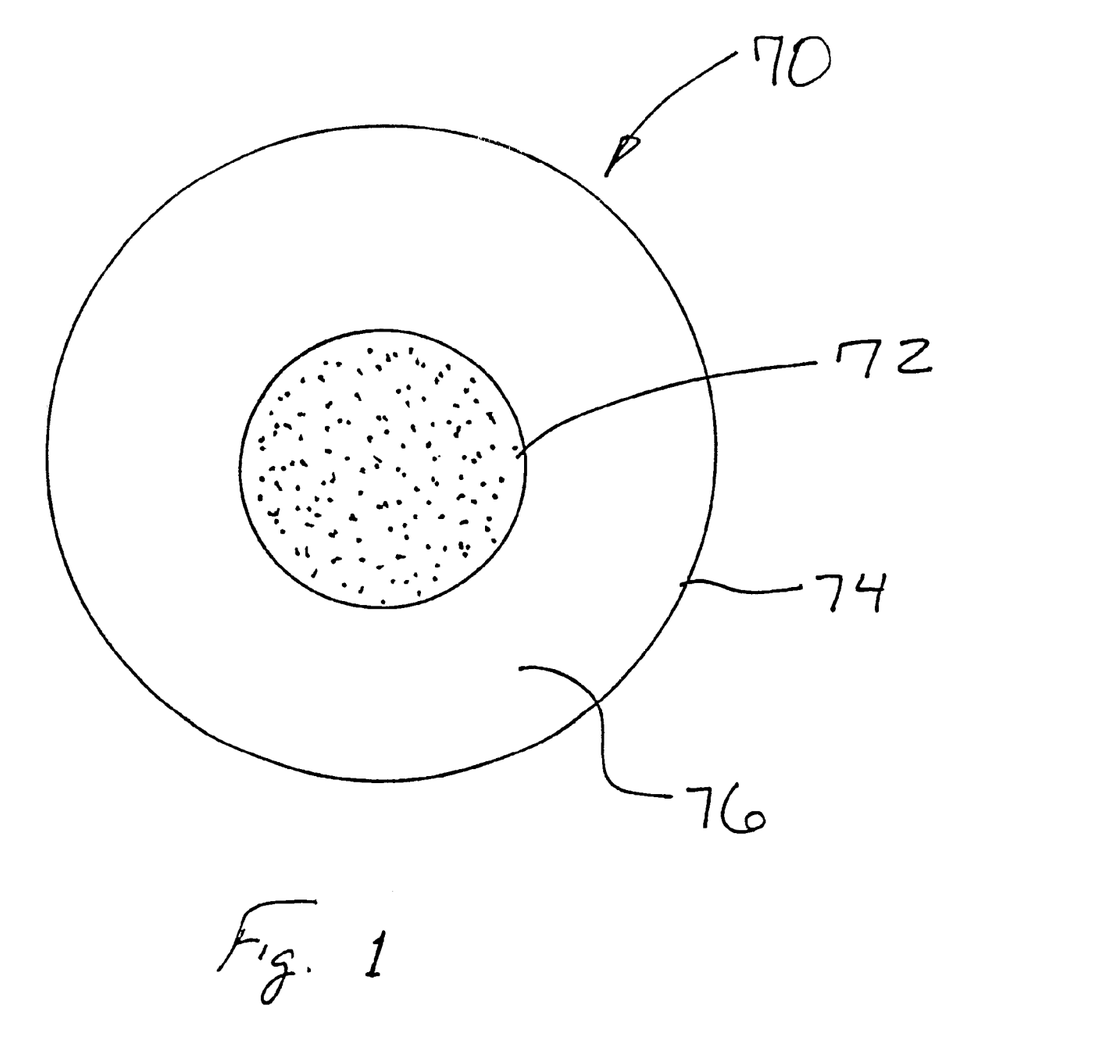
FIG. 1 is a plan view of a sealed dressing useful for applying the topical anesthetic of the present invention.

One contemplated manner of applying the Tetracaine-based anesthetic solution, as shown in FIG. 1, is to employ a sealed dressing 70 comprising an absorbent pad 72 that is centrally attached to a securing sheet 74. Pad 72 may comprise a material that, when wetted, undergoes a partial phase change into a material having a gelatinous consistency, such as polyvinyl acetate. The pad 72 is soaked with the Tetracaine-based anesthetic solution and the dressing 70 is placed on the skin, with the pad 72 contacting the region to be anesthetized. The securing sheet 74 is preferably tightly, but releasably secured to the skin surrounding the region to be anesthetized and is preferably formed of an air-impervious material to prevent evaporation of the pad 72. In addition, the sheet 74 should be made from a skin-tolerant material that is not soluble in alcohol. The surface 76 of the sheet 74 surrounding the pad 72 may include a releasable adhesive that is not dissolved by alcohol to permit the sheet to be releasably adhered to the skin. When anesthesia is effected after the soaked pad 72 has been maintained in contact with the indicated region for a prescribed period, the dressing 70 can be removed, and subsequent medical procedures can be performed at the region.

Delivering a topical solution, such as the Tetracaine-based anesthetic solution, within a bodily cavity, such as the tympanic membrane and the inner wall of the ear canal, can be problematic. The canal is narrow and curved, thus making maneuvering into the canal a difficult and delicate procedure. In addition, to anesthetize the ear canal and tympanic membrane, the solution must be maintained in wet contact with the ear canal wall and tympanic membrane for a sufficient time to effect anesthetization. Accordingly, an anesthetic solution is preferably delivered into the canal with an expandable, absorbent applicator, such as a sponge.

Figure 2:
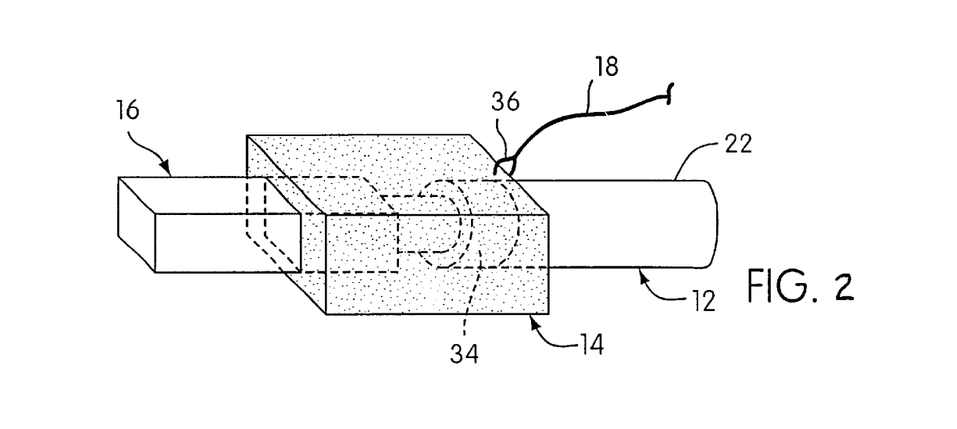
FIG. 2 is an enlarged perspective view of a compressed fluid applicator element and a plug attached to an applicator inserting and soaking device of the apparatus of the present invention.

FIG. 2 shows a dry, compressed applicator 14 in conjunction with an applicator insertion and soaking device 12, to be described below. When dry, the applicator 14 can be compressed into a small and compact configuration in which it remains until wetted. The small, compact configuration of the applicator 14 permits the applicator to be easily inserted into an ear canal. When the applicator is wetted, it becomes expanded—as shown by applicator 14' in FIG. 3—to a size that is significantly larger than that of the compressed applicator 14. The expanded applicator 14' is preferably cylindrical, so as to generally conform to the inner walls of the ear canal, and preferably has an outer diameter that is larger than the diameter of a typical ear canal, so that the outer surface of the expanded applicator 14' is in complete, conforming contact with the inner walls of the ear canal. The applicator 14(14') may also have a hollow central portion 34 to accommodate an applicator insertion and soaking device, as will become apparent in the description of that device below, but the applicator 14(14') need not necessarily be hollow.

Figure 4:
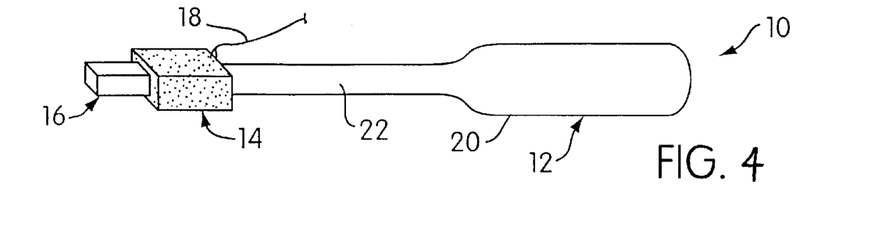
FIG. 4 is a perspective view of an apparatus for anesthetizing the ear canal and ear drum in accordance with a method of the present invention.

In the preferred embodiment, the applicator 14(14') comprises a sponge made of a compressible, skin-tolerant material, such as polyvinyl acetate. Further, as shown in FIG. 2 and 4, a withdrawal tether 18 is secured to an end (the distal end) of the applicator 14(14'). Tether 18 is preferably a silk thread passed through a hole formed in an outer wall of the applicator 14(14') and knotted thereat. In the most preferred manner of carrying out the method of the present invention, applicator 14 (14') comprises a polyvinyl acetate sponge of the type available from Xomed of Jacksonville, Fla. under the trade name "Schindler's Ear Pack".

To apply the Tetracaine-based solution to the ear canal and the tympanic membrane, the dry compressed applicator 14 is first partially wetted with anesthetic solution at one end thereof (the insertion end) to partially expand, and thereby soften, the insertion end. The partially wetted applicator is then inserted into the ear canal with a suitable slender, elongated instrument, such as a tweezers. Alternatively, a few drops of anesthetic solution can be first placed at the entrance of the ear canal, and the dry applicator 14 can be inserted into the ear canal, at which point it absorbs the solution previously placed in the ear, thus wetting and softening the insertion end of the applicator. Although the insertion end is preferably wetted and softened in the manner just described, the applicator could be inserted into the ear canal in a completely dry, compressed state, but ease of insertion and patient comfort may be compromised.

Using a suitable instrument, the applicator 14 is then advanced into the ear canal until contacts or is adjacent to the tympanic membrane. When the applicator is fully inserted, a fluid-injecting instrument (e.g. a dropper) may be used to inject additional anesthetic solution into the ear canal and against the proximal end of the applicator, opposite the insertion end. The applicator, being absorbent, wicks the solution from the proximal end throughout the body of the applicator, thus soaking and fully expanding the entire applicator.

After a prescribed anesthetizing period, the expanded applicator 14' is withdrawn from the ear canal using the withdrawal tether 18, the end of which remains outside the ear canal during the anesthetizing procedure. Because the outer surface of the expanded applicator 14' is in conforming contact with the inner wall of the ear canal, and especially if a Tetracaine-based anesthetic solution with an alcohol solvent is used, the applicator actually cleanses the inner walls of the ear canal when withdrawn. The ear canal and tympanic membrane are now anesthetized and ready for subsequent medical procedures.

An apparatus for anesthetizing the ear canal and ear drum according to the present invention is indicated generally by the reference number 10 in FIG. 4. The apparatus 10 constitutes one example of a delivery system for delivering a topical anesthetic, such as the Tetracaine-based anesthetic solution described above, to the ear canal and tympanic member. In the illustrated embodiment, the apparatus 10 includes an applicator inserting and soaking device 12 with a compressed applicator 14 secured to an end thereof. An applicator withdrawal tether 18 is attached to the applicator 14 and a plug 16 is inserted through a distal end of the applicator 14 and into a distal end 32 of the applicator inserting and soaking device 12.

Figure 5:
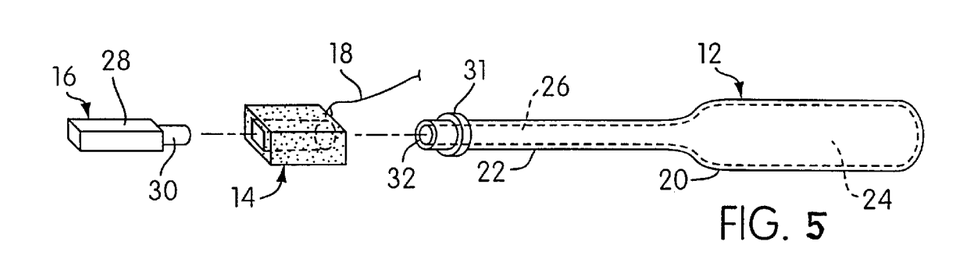
FIG. 5 is an exploded perspective view of the apparatus of FIG. 4.

As shown in FIGS. 4 and 5, the applicator inserting and soaking assembly 12 preferably includes an enlarged handle portion 20 and an elongated insertion portion 22 extending from an end of the handle portion 12. In the preferred embodiment, the handle 20 and insertion portion 22 are integrally formed by injection molding a relatively rigid, nonreactive plastic that is not soluble in alcohol. The elongated portion 22 is hollow, thus defining a conduit 26 extending therethrough to a distal opening at the distal end 32 of the insertion portion 22. Similarly, the handle 20 is preferably also hollow and enlarged with respect to the insertion portion 22, thus defining a reservoir 24 inside the handle 20 for containing a fluid. The handle 20 is flexible, thus functioning as a fluid-forcing mechanism, whereby the handle 20 can be compressed between the thumb and finger to force fluid from the reservoir 24 and through the conduit 26.

As shown in FIG. 5 the applicator 14, which preferably comprises an absorbent compressible sponge of polyvinyl acetate, as describe above, is compressed onto the distal end 32 of the elongated insertion portion 22. Prior to compressing the applicator 14 onto the insertion portion 22, a removable plug 16, comprising an enlarged grippable portion 28 with a cylindrical extension 30, is inserted into the distal end 32 of the conduit 26 for a distance of 2 to 4 mm. If necessary, a thin, breakable plastic seal can be created at a location along the conduit 26 of the insertion portion 22 to prevent premature leakage.

Figure 3:
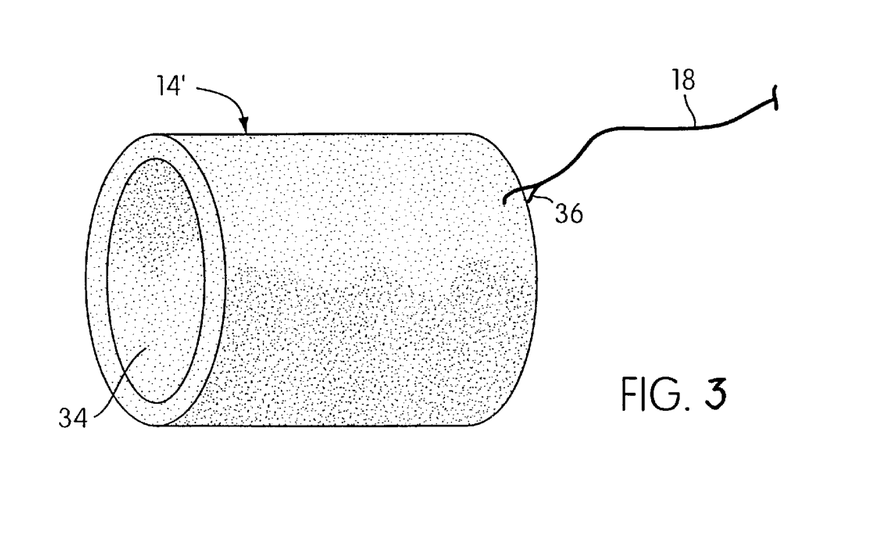
FIG. 3 is an enlarged perspective view of an expanded fluid applicator element and applicator withdrawal tether attached thereto.

With the applicator 14 in a dried condition, it is squeezed under a vacuum or pressure to a rigid, compressed state that is maintained until the applicator 14 is wetted by a liquid. In the preferred embodiment, the applicator 14 is compressed to a solid, generally rectangular shape having cross-sectional dimensions of about 3 mm×3 mm, and a length of about 12 to 14 mm. As shown in FIG. 3, when the applicator is sufficiently wetted, it expands into a structure such as 14' preferably having a generally cylindrical shape with an opening 34 extending therethrough. The expanded applicator 14 has a length of about 15 mm and measures about 10 mm in outer diameter and 6 mm in inner diameter with a wall thickness of about 2 mm. The expanded applicator 14' has a preferred pore size of 10 to 50 microns.

A volume of fluid, such as the Tetracaine-based anesthetic solution, is stored in the reservoir 24 and is held within the reservoir 24 and conduit 26 by the plug 16. Alternatively, the Tetracaine powder and associated solvent may be provided separately and mixed in the reservoir 24 just prior to application, or they may be both provided in the reservoir 24, but separated by a membrane which can be broken, for example by squeezing the handle 20, to mix the Tetracaine powder and alcohol solvent, thus dissolving the powder.

Figure 6:
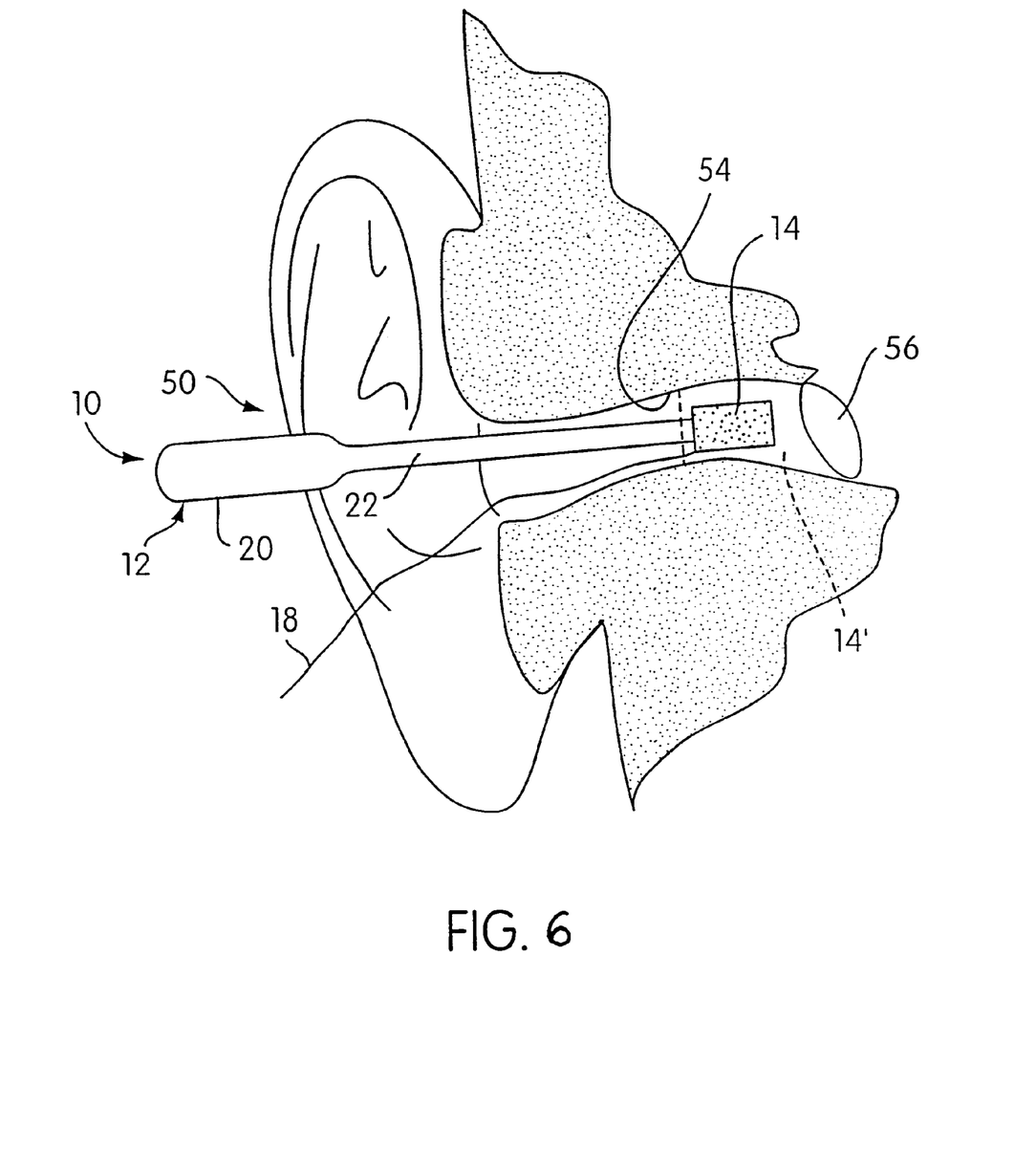
FIG. 6 is a cross-sectional view of a human ear canal and tympanic membrane (i.e. ear drum) with an apparatus according to the present invention inserted into the canal and showing the fluid applicator in both the compressed and expanded states.

A method of applying an anesthetic agent to the ear canal and tympanic membrane with the apparatus 10 is shown in FIG. 6. Although FIG. 6 depicts a cross section of a human ear structure 50, it is to be understood that the anesthetic, method, and apparatus of the present invention could be used in veterinary applications as well. The plug 16 is removed from the distal end 32 of the insertion portion 22, and a small amount of solution is squeezed from the reservoir 24 to partially wet and soften the insertion end of the applicator 14 secured toe the distal end 32 of the insertion portion 22. Initially, only the insertion, or distal, end of the applicator 14 is wetted, thus softening the applicator 14 and facilitating further insertion thereof with the insertion portion 22. A radially extending peripheral collar 31 (see FIG. 5) may be provided on the insertion portion 22 near its distal end 32 to prevent the applicator 14 from sliding up the insertion portion 22 as the insertion portion 22 is advanced into the ear canal. The applicator 14 is preferably inserted into the ear canal 54 until it contacts or is adjacent to the tympanic membrane 56. As the wet soft applicator 14 is advanced into the ear drum 54, more anesthetic may be applied by squeezing the fluid forcing mechanism of the handle 20 to further soak the applicator 14. The applicator 14, having now been soaked by the anesthetic solution, attains its expanded state 14' whereupon the hollow opening 34 through the expanded applicator 14' becomes larger than the outer diameter of the insertion portion 22. Thus, the insertion portion 22, and indeed the entire applicator inserting and soaking device 12, is released from the expanded applicator 14'. The applicator inserting and soaking device 12 is then withdrawn from the ear canal 54 with The soaked applicator 14' left in place so as to anesthetize the ear canal 54 and the tympanic membrane 56. Friction between the walls of the ear canal and the expanded applicator 14' would retain the applicator 14' when the device is withdrawn. Therefore, it is not absolutely necessary that the diameter of opening 34 be larger than the outside diameter of insertion portion 22. The soaked applicator 14' is left inside the ear canal 54 for a prescribed anesthetizing period, e.g., from 15–30 minutes, after which time the applicator 14 is withdrawn using the applicator withdrawal tether 18.

A fluid-forcing mechanism other than squeezable handle 20 may be employed. For example, the fluid reservoir may comprise a hollow cylinder (not shown) connected at one end thereof to a tube constituting or connected to a conduit of an elongated applicator insertion instrument to which the applicator is releasably secured, and a syringe-like plunger can be inserted into an opposite end of the cylinder for manually forcing a desired amount of anesthetic solution from the cylinder into the conduit.

Figure 7:
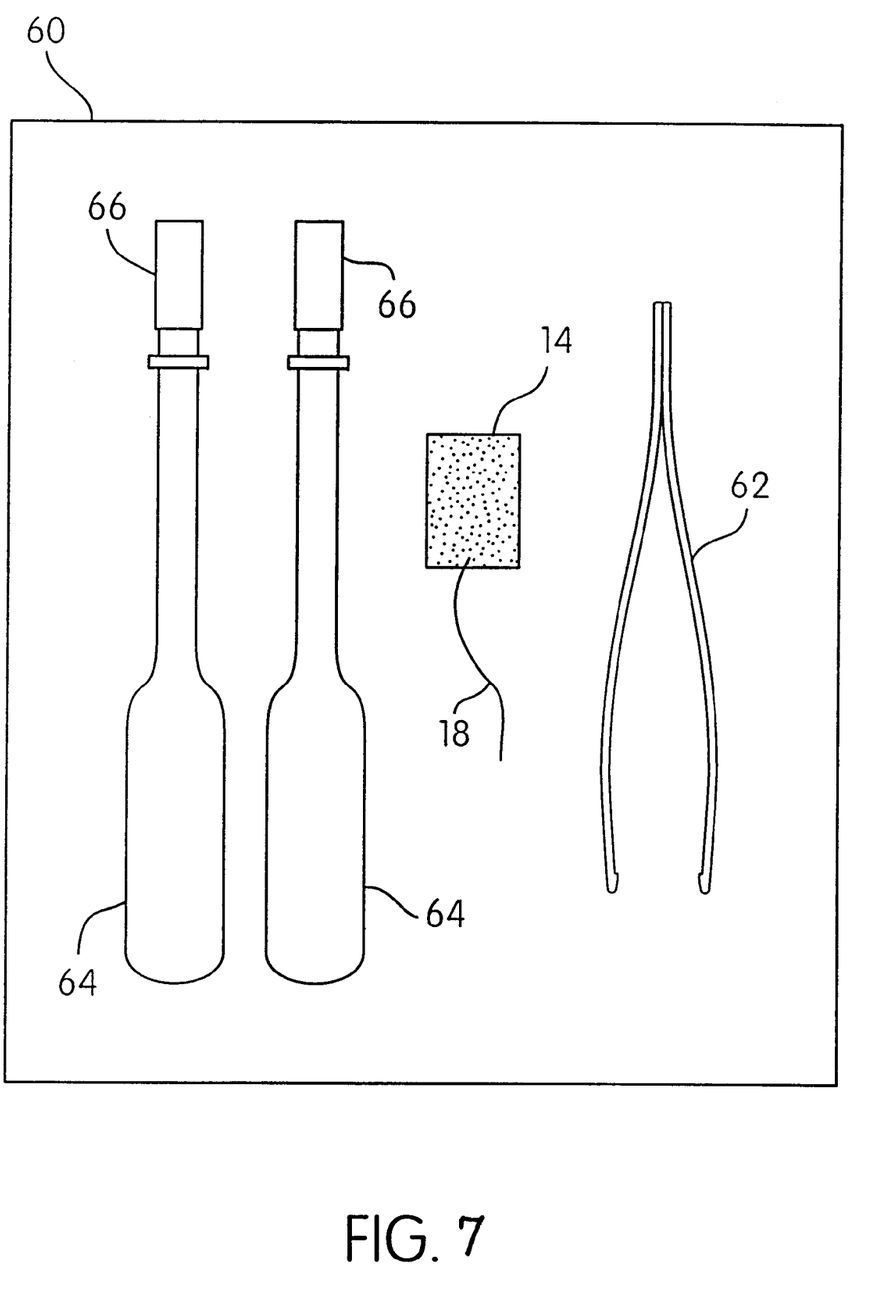
FIG. 7 is a schematic view of a kit containing instruments for anesthetizing the ear canal and ear drum according to the method of the present invention.

The compressed applicator 14 need not necessarily be pre-attached to a soaking and insertion device. As described above, the applicator 14 can partially wetted outside the ear canal, inserted into the ear canal with a narrow elongated instrument, such as a tweezers, and fully wetted inside the ear canal using a fluid-injecting device. such as a dropper. To that end, a kit 60 for performing the presently-described method for anesthetizing the ear canal and tympanic membrane is schematically shown in FIG. 7. The kit 60 includes a tweezers 62, a compressed applicator 14 with a withdrawal tether 18 attached thereto, and a pair of fluid-injecting devices 64 having plugs 66 inserted into the distal ends thereof. The devices 64 may be identical to the applicator inserting and soaking device 10 shown in FIGS. 4, 5, and 6 and described above. Each of the fluid-injecting devices 64 would include a reservoir containing an amount of anesthetic solution. Of course one device 64 will suffice if its reservoir has sufficient capacity to accommodate enough anesthetic solution for performing the anesthetizing procedure. Further, the anesthetic solution may be stored premixed in the reservoir(s) or in another container from which it is transferred into the reservoir(s) prior to use, or the constituents of the anesthetic solution may be stored unmixed in separate containers or in the reservoir(s) separated by a breakable membrane.

The contents of one of the fluid-injecting devices 64 can be used to pre-wet the applicator 14 or can be placed directly into the ear canal. The applicator 14 is then placed in the ear canal using the tweezers 62 and is then advanced and further wetted using the contents of the other fluid-injecting device (or alternatively, the remaining contents of the first fluid-injecting device) to completely soak and expand the applicator using the other fluid-injecting device 64. After the soaked and expanded applicator has been in the ear canal for a sufficient period to effect the desired level of anesthetization, the applicator is withdrawn using the withdrawal tether 18.

Figure 8:
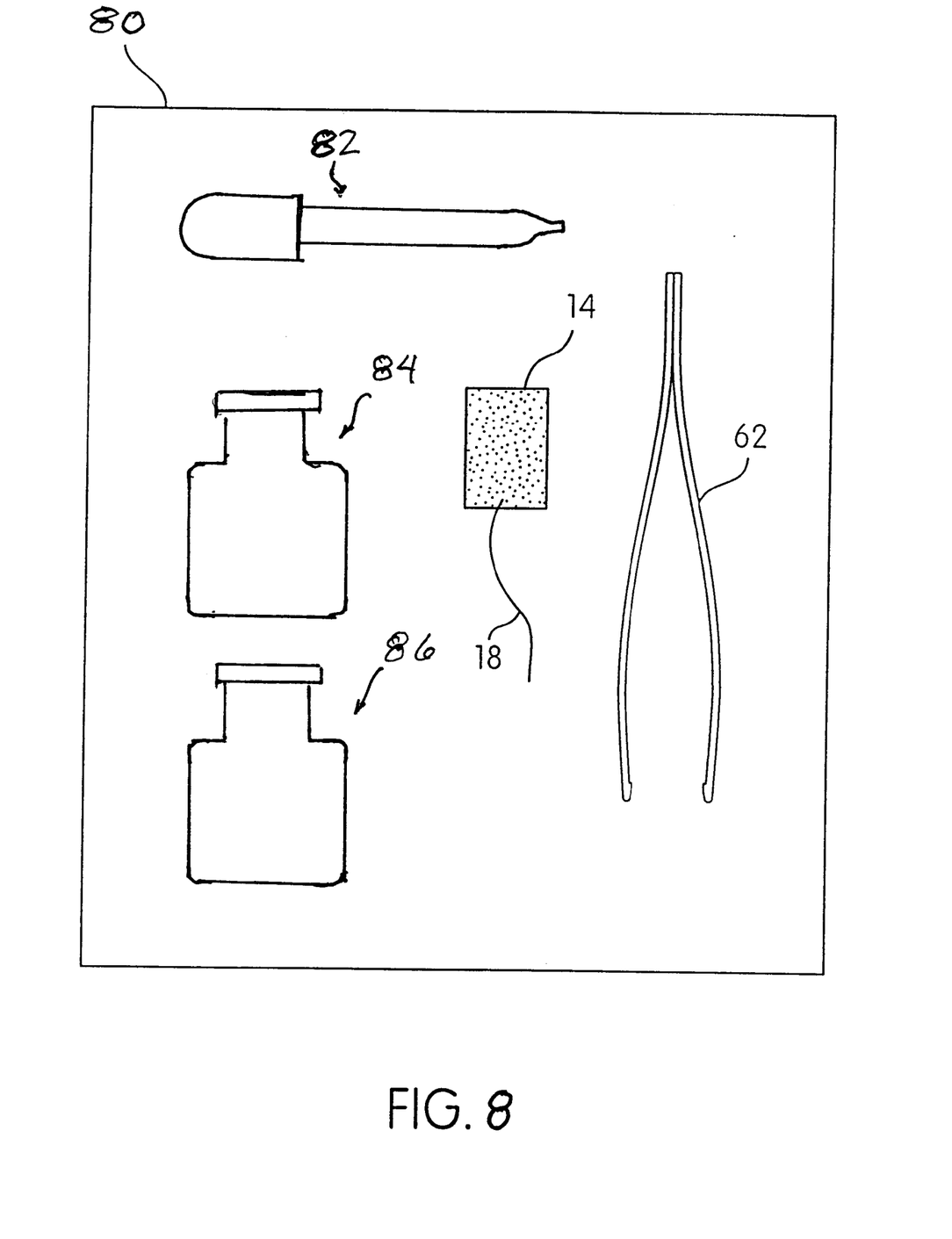
FIG. 8 is a schematic view of a second embodiment of a kit containing materials and instruments for anesthetizing the ear canal and ear drum according to the method of the present invention.

A second embodiment of a kit for performing the anesthetizing procedure of the present invention is designated generally by reference number 80 in FIG. 8. The kit 80 includes a tweezers 62 and an applicator 14, preferably a dry, compressed sponge of polyvinyl acetate with a tether 18, as described above. The kit 80 further includes an eyedropper 82 and containers, e.g., vials, 84 and 86, which contain a tetracaine base powder and a measured aliquat of solvent, such as isopropyl alcohol, respectively. The kit 80 is preferably packaged as a single sterile unit.

The physician mixes the tetracaine base powder with the solvent and uses the eyedropper 82 to deliver a small amount of the anesthetic solution into the ear canal. The applicator 14 is then inserted into the ear canal using the tweezers 62, and, after the applicator 14 is fully inserted, the remainder of the anesthetic solution is added into the ear canal with the eyedropper 82 to fully wet and expand the applicator 14. After a period of time sufficient to effect anesthesia, the applicator 14 is withdrawn from the ear canal, either with the tether 18 or with the tweezers 62.

While the invention has been described in connection with what are presently considered to be the most practical and preferred embodiments, it is to be understood that the invention is not to be limited to the disclosed embodiments, but on the contrary is intended to cover various modifications and equivalent arrangements included within the spirit and scope of the appended claims.

What is claimed is:

1. An apparatus for applying a fluid to the ear canal and tympanic membrane, said apparatus comprising:

an expandable absorbent applicator shaped to be fully insertable into the ear canal, said applicator being constructed and arranged to maintain a compressed configuration when in a dry state and to expand when in a fluid-soaked state;

an applicator withdrawal tether attached to said applicator and constructed and arranged to facilitate withdrawal of said applicator from an ear canal into which said applicator has been inserted; and an applicator inserting and soaking device including:

an elongated insertion portion constructed and arranged to permit said applicator to be releasably secured to a distal end of said insertion portion for inserting said applicator into an ear canal by inserting said insertion portion into the ear canal distal-end-first with the applicator releasably secured to the distal end, said elongated insertion portion defining a conduit for carrying a fluid to said applicator secured to the distal end of said insertion portion;

a fluid reservoir in fluid communication with said conduit for holding an amount of fluid; and a fluid forcing mechanism constructed and arranged to force fluid from said fluid reservoir into said conduit to wet said applicator secured to the distal end of said insertion portion.

2. The apparatus of claim 1, wherein said applicator comprises a sponge made of polyvinyl acetate.

3. The apparatus of claim 1, wherein said applicator has an opening formed therein and is releasably secured to the distal end of said insertion portion by inserting the distal end into the opening and compressing said applicator onto the distal end so that said applicator is frictionally secured to the distal end.

4. The apparatus of claim 3, wherein the opening formed in the applicator is larger than an outer width dimension of said insertion portion when said applicator is in the fluid-soaked expanded state, so that said insertion portion and said applicator can be easily separated from one another when the applicator is in the wet expanded state.

5. The apparatus of claim 1, wherein said applicator inserting and soaking device comprises:

a tubular portion defining said insertion portion; and an enlarged hollow portion integrally formed with said tubular portion and defining said fluid reservoir, said enlarged hollow portion being formed of a flexible material thereby permitting said enlarged hollow portion to be manually compressed to force fluid from said enlarged hollow portion and into said tubular portion.

6. The apparatus of claim 1, further comprising a plug removably inserted into a distal end opening of said insertion portion to prevent escape of fluid from said conduit and said reservoir.

7. The apparatus of claim 1, further comprising an amount of tetracaine-based topical anesthetic solution contained within said fluid reservoir.

8. The apparatus of claim 7, wherein said Tetracaine-based topical anesthetic substance comprises a powder to be dissolved by a solvent to form a topical anesthetic solution.

9. The apparatus of claim 7, wherein said Tetracaine-based topical anesthetic substance comprises a topical anesthetic solution including Tetracaine dissolved in a solvent.

10. A method of anesthetizing the ear canal and the tympanic membrane using a topical anesthetic solution, said method comprising:

providing an expandable absorbent applicator in a dry, compressed condition, the applicator being constructed and arranged to expand when wetted;

providing an anesthetic solution dissolved in a solvent;

inserting the applicator in a dry, compressed condition or a partially wetted, partially expanded condition into the ear canal and advancing the applicator into the ear canal to a position contacting or adjacent to the tympanic membrane;

applying the anesthetic solution via an elongated insertion member defining a conduit to the applicator to wet the entire applicator and cause the applicator to fully expand, so that an outer surface of the applicator and the anesthetic solution absorbed by the applicator are in contact with the inner walls of the ear canal and the tympanic membrane; and leaving the expanded applicator in the ear canal for a period of time sufficient to attain a desired level of anesthetization of the ear canal and tympanic membrane.

11. A method of anesthetizing the ear canal and the tympanic membrane using a topical anesthetic solution, said method comprising:

providing an apparatus for applying a topical anesthetic solution to the ear canal and tympanic membrane, said apparatus comprising:

an expandable absorbent applicator, said applicator being constructed and arranged to maintain a compressed configuration when in a dry state and to expand when in a fluid-soaked state;

an applicator withdrawal tether attached to said applicator and constructed and arranged to facilitate withdrawal of said applicator from an ear canal into which said applicator has been inserted; and an applicator inserting and soaking device including:

an elongated insertion portion constructed and arranged to permit said applicator to be releasably secured to a distal end of said insertion portion for inserting said applicator into an ear canal by inserting said insertion portion into the ear canal distal-end-first with the applicator releasably secured to the distal end, said elongated insertion portion defining a conduit for carrying a fluid to said applicator secured to the distal end of said insertion portion;

a fluid reservoir in fluid communication with said conduit for holding an amount of fluid; and a fluid forcing mechanism constructed and arranged to force fluid from said fluid reservoir into said conduit to wet said applicator secured to the distal end of said insertion portion;

providing, within said fluid reservoir, an anesthetic solution comprising Tetracaine dissolved in a solvent;

releasably securing said applicator to the distal end of said insertion portion;

inserting said applicator in a dry, compressed condition or a partially wetted, partially expanded condition into the ear canal and advancing the applicator into the ear canal with said insertion portion to a position contacting or adjacent to the tympanic membrane;

wetting the entire applicator with the anesthetic solution by forcing the anesthetic solution from the reservoir with the fluid forcing mechanism to cause the solution to flow through the conduit of the insertion portion and to the applicator to cause the applicator to fully expand, so that an outer surface of the applicator and the anesthetic solution absorbed by the applicator are in contact with the inner walls of the ear canal and the tympanic membrane;

removing the applicator inserting and soaking device from the ear canal, thereby separating the expanded applicator from the distal end of the insertion portion and leaving the expanded applicator in the ear canal for a period of time sufficient to attain a desired level of anesthetization of the ear canal and tympanic membrane; and withdrawing the expanded applicator from the ear canal with the applicator withdrawal tether after the period of time.

* * * * *